(12) United States Patent
Mayer

(10) Patent No.: US 6,177,037 B1
(45) Date of Patent: Jan. 23, 2001

(54) METHOD OF FORMING A SLIT IN A RESEAL ELEMENT FOR A NEEDLELESS INJECTION SITE

(75) Inventor: Bruno Franz P. Mayer, Orange, CA (US)

(73) Assignee: Becton, Dickinson and Company, Franklin Lakes, NJ (US)

( * ) Notice: Under 35 U.S.C. 154(b), the term of this patent shall be extended for 0 days.

(21) Appl. No.: 09/182,369

(22) Filed: Oct. 29, 1998

Related U.S. Application Data

(63) Continuation-in-part of application No. 09/137,581, filed on Aug. 21, 1998, which is a continuation-in-part of application No. 08/966,337, filed on Nov. 7, 1997, which is a continuation-in-part of application No. 08/735,217, filed on Oct. 22, 1996, now Pat. No. 5,836,923, which is a continuation-in-part of application No. 08/699,848, filed on Aug. 20, 1996, now Pat. No. 5,820,601, which is a continuation-in-part of application No. 08/493,744, filed on Jun. 22, 1995, now Pat. No. 5,616,130, which is a continuation-in-part of application No. 08/401,854, filed on Mar. 10, 1995, now Pat. No. 5,616,129, which is a continuation-in-part of application No. 08/262,994, filed on Jun. 20, 1994, now Pat. No. 5,470,319.

(51) Int. Cl.[7] .................................................. B26D 7/04
(52) U.S. Cl. ................................ 264/155; 83/19; 83/30; 83/660; 264/334; 425/290; 425/298
(58) Field of Search ................................. 83/19, 30, 660; 264/155, 154, 334; 425/290, 298

(56) References Cited

U.S. PATENT DOCUMENTS

| 3,977,555 | 8/1976 | Larson ................................. 215/247 |
| 4,063,460 | 12/1977 | Svensson ............................. 73/425.6 |
| 4,134,512 | 1/1979 | Nugent ................................. 215/247 |
| 4,181,051 | * 1/1980 | Drori . |
| 4,246,899 | 1/1981 | Loseff ................................... 128/276 |
| 4,301,936 | 11/1981 | Percarpio ............................. 215/247 |
| 4,338,764 | 7/1982 | Percarpio ............................... 53/432 |
| 4,655,752 | 4/1987 | Honkanen et al. ................... 604/256 |
| 4,838,855 | 6/1989 | Lynn ....................................... 604/49 |
| 4,874,377 | 10/1989 | Newgard et al. ..................... 604/167 |
| 5,064,416 | 11/1991 | Newgard et al. ..................... 604/167 |
| 5,100,394 | 3/1992 | Dudar et al. .......................... 604/283 |
| 5,122,123 | 6/1992 | Vaillancourt ......................... 604/192 |
| 5,122,129 | 6/1992 | Olson et al. .......................... 604/905 |
| 5,135,489 | 8/1992 | Jepson et al. ........................... 604/48 |
| 5,154,703 | 10/1992 | Bonaldo ............................... 604/244 |

(List continued on next page.)

FOREIGN PATENT DOCUMENTS

| 2001732 | 4/1990 | (CA) . |
| 3105437 A1 | 10/1982 | (DE) . |
| 0309771 A1 | 5/1989 | (EP) . |
| 0544581 A1 | 11/1991 | (EP) . |
| 93/05838 | 4/1993 | (WO) . |
| 93/05839 | 4/1993 | (WO) . |
| 93/11828 | 6/1993 | (WO) . |
| 9600107 | 6/1994 | (WO) . |
| 97/21464 | 6/1997 | (WO) . |

*Primary Examiner*—Jan H. Silbaugh
*Assistant Examiner*—Mark Eashoo
(74) *Attorney, Agent, or Firm*—Eric M. Lee, Esq.

(57) ABSTRACT

A method of forming a slit in a reseal element having an outer surface defined by a proximal end thereof, a semi-spherical inner surface portion defined by a dome region of the proximal end, and an annular inner surface portion which circumvents the semi-spherical inner surface portion. The method is accomplished through the use of a cutting assembly which includes a locator plate having a locator cavity disposed therein, a cutting core, a support fixture, and a blade member. The method comprises the initial step of inserting the reseal element into the locator cavity of the locator plate. Thereafter, the dome region of the reseal element is pre-stressed by the contact of the support fixture thereagainst, with the blade member then being advanced upwardly through the proximal end of the reseal element to form the slit therein.

9 Claims, 3 Drawing Sheets

U.S. PATENT DOCUMENTS

| | | | |
|---|---|---|---|
| 5,158,554 | 10/1992 | Jepson et al. | 604/283 |
| 5,171,234 | 12/1992 | Jepson et al. | 604/283 |
| 5,188,620 | 2/1993 | Jepson et al. | 604/283 |
| 5,201,725 | 4/1993 | Kling | 604/284 |
| 5,203,775 | 4/1993 | Frank et al. | 604/256 |
| 5,207,661 | 5/1993 | Repschlager | 604/317 |
| 5,215,538 | 6/1993 | Larkin | 604/249 |
| 5,234,413 | 8/1993 | Wonder et al. | 604/248 |
| 5,242,425 | 9/1993 | White et al. | 604/256 |
| 5,242,432 | 9/1993 | Defrank | 604/284 |
| 5,250,033 | 10/1993 | Evans et al. | 604/160 |
| 5,269,771 | 12/1993 | Thomas et al. | 604/213 |
| 5,273,533 | 12/1993 | Bonaldo | 604/83 |
| 5,286,453 | 2/1994 | Pope | 422/100 |
| 5,324,256 | 6/1994 | Lynn et al. | 604/49 |
| 5,336,192 | 8/1994 | Palestrant | 604/167 |
| 5,351,383 * | 10/1994 | Behnke et al. . | |
| 5,360,012 | 11/1994 | Ebara et al. | 128/764 |
| 5,360,413 | 11/1994 | Leason et al. | 604/249 |
| 5,380,306 | 1/1995 | Brinon | 604/244 |
| 5,401,245 | 3/1995 | Haining | 64/86 |
| 5,439,451 | 8/1995 | Collinson et al. | 604/247 |
| 5,470,319 | 11/1995 | Mayer | 604/167 |
| 5,474,544 | 12/1995 | Lynn | 604/283 |
| 5,487,728 | 1/1996 | Vaillancourt | 604/86 |
| 5,501,426 | 3/1996 | Atkinson et al. | 251/491 |
| 5,509,912 | 4/1996 | Vaillancourt et al. | 604/283 |
| 5,514,116 | 5/1996 | Vaillancourt et al. | 604/283 |
| 5,520,665 | 5/1996 | Fleetwood | 604/283 |
| 5,520,666 | 5/1996 | Choudhury et al. | 604/283 |
| 5,549,566 | 8/1996 | Elias et al. | 604/167 |
| 5,549,577 | 8/1996 | Siegel et al. | 604/256 |
| 5,578,059 | 11/1996 | Patzer | 604/249 |
| 5,603,882 * | 2/1997 | Takano et al. . | |
| 5,616,129 | 4/1997 | Mayer | 604/167 |
| 5,616,130 | 4/1997 | Mayer | 604/167 |
| 5,620,434 | 4/1997 | Brony | 604/406 |
| 5,669,891 | 9/1997 | Vaillancourt | 604/283 |
| 5,685,866 | 11/1997 | Lopez | 604/249 |
| 5,688,254 | 11/1997 | Lopez et al. | 604/283 |
| 5,690,612 | 11/1997 | Lopez et al. | 604/93 |
| 5,694,686 | 12/1997 | Lopez | 29/890.126 |
| 5,695,466 | 12/1997 | Lopez et al. | 604/93 |
| 5,699,821 | 12/1997 | Paradis | 137/1 |
| 5,700,248 | 12/1997 | Lopez | 604/249 |
| 5,774,972 * | 7/1998 | Ehrlich . | |
| 5,820,601 * | 10/1998 | Mayer . | |
| 5,836,923 * | 11/1998 | Mayer . | |

* cited by examiner

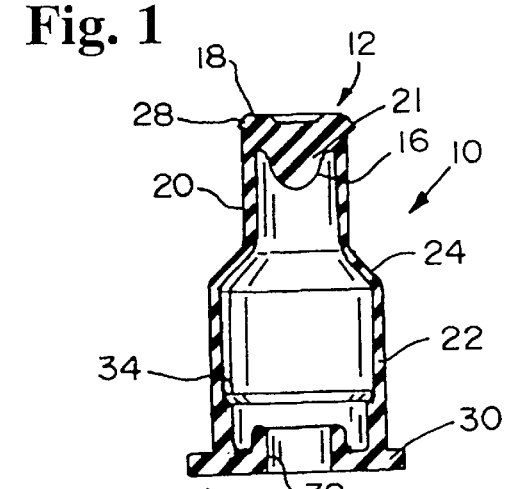
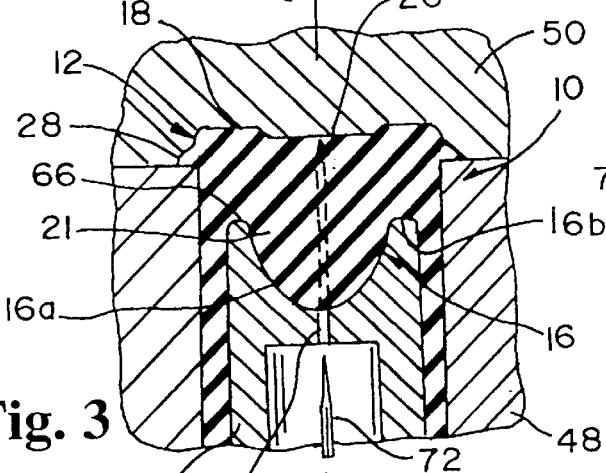
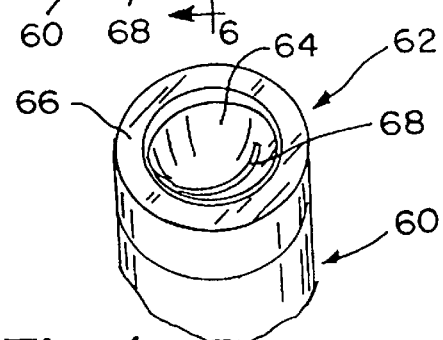
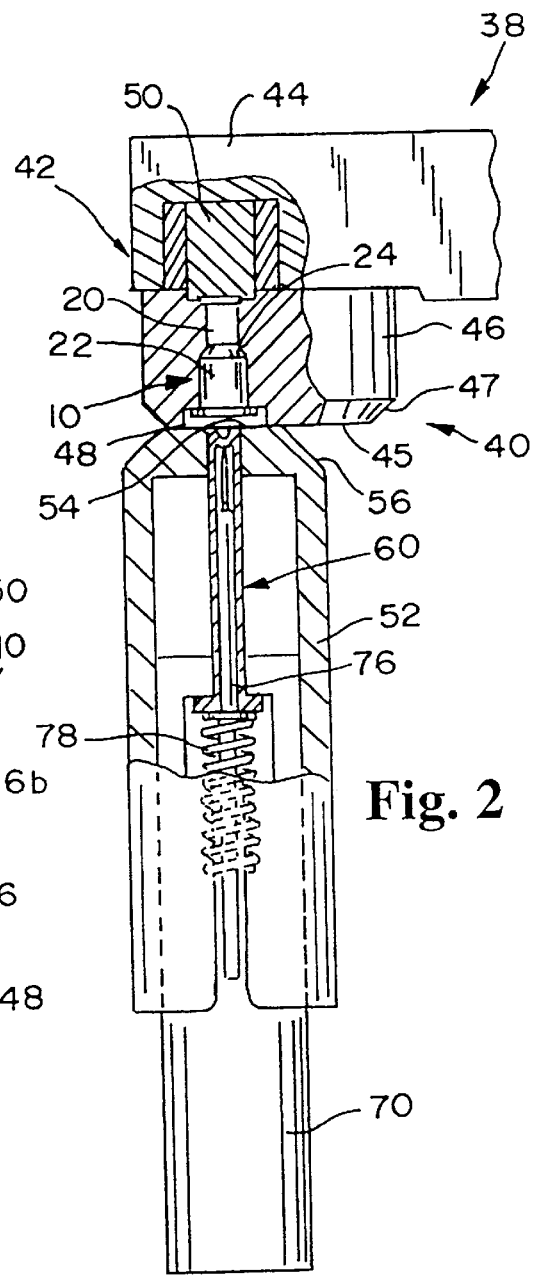
Fig. 1
Fig. 2
Fig. 3
Fig. 4

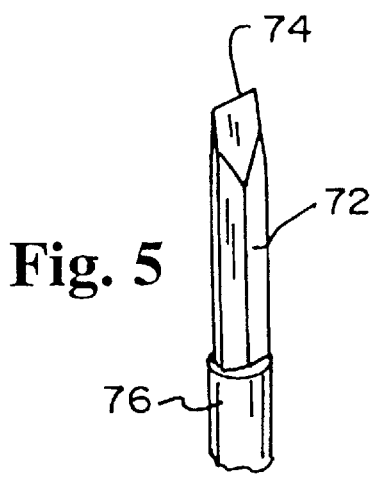
Fig. 5
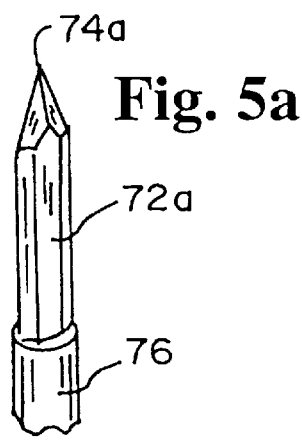
Fig. 5a
Fig. 6
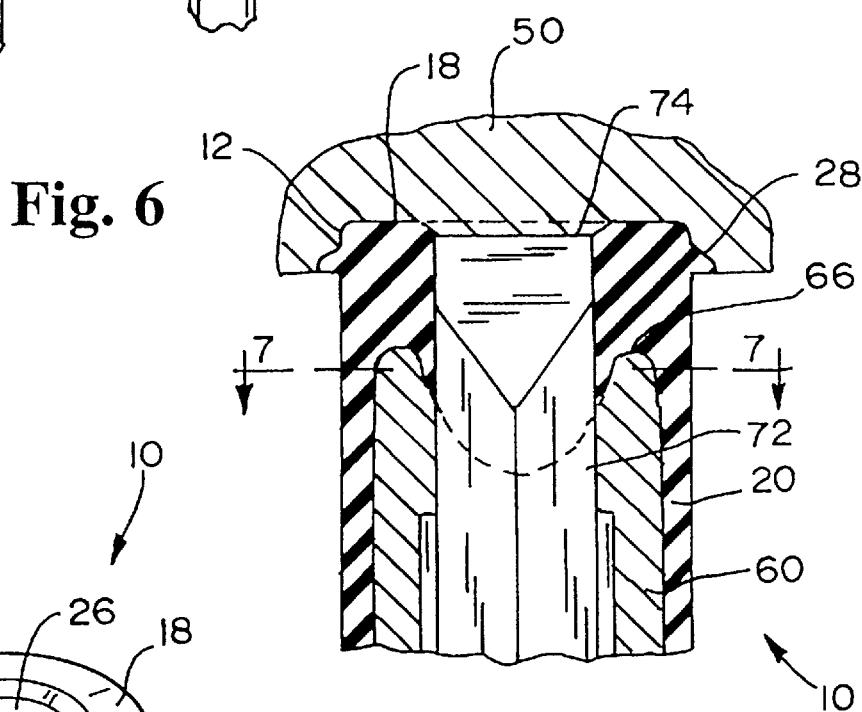
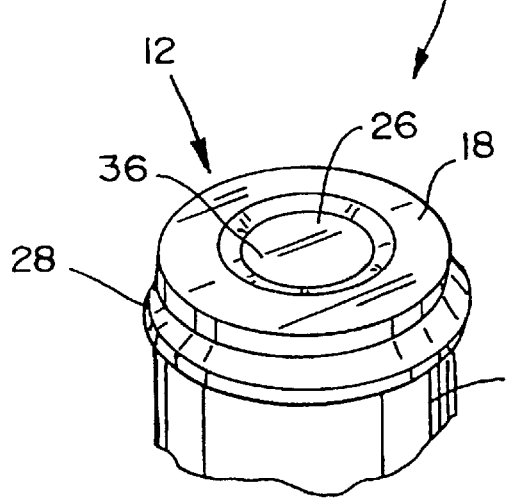
Fig. 8
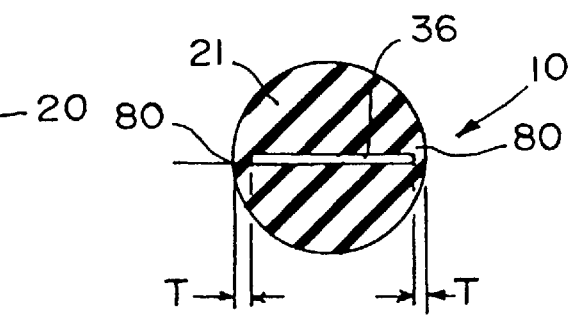
Fig. 7

METHOD OF FORMING A SLIT IN A
RESEAL ELEMENT FOR A NEEDLELESS
INJECTION SITE

This application is a continuation-in-part of Ser. No. 09/137,581, Aug. 21, 1998, which is a continuation-in-part of Ser. No. 08/966,337, Nov. 07, 1997, which is a continuation-in-part of Ser. No. 08/735,217, Oct. 22, 1996, U.S. Pat. No. 5,836,923, which is a continuation-in-part of Ser. No. 08/699,848, Aug. 20, 1996, U.S. Pat. No. 5,820,601, which is a continuation-in-part of Ser. No. 08/493,744, Jun. 22, 1995, U.S. Pat. No. 5,616,130, which is a continuation-in-part of Ser. No. 08/401,854, Mar. 10, 1995, U.S. Pat. No. 5,616,129, which is a continuation-in-part of Ser. No. 08/262,994, Jun. 20, 1994, U.S. Pat. No. 5,470,319.

FIELD OF THE INVENTION

The present invention relates generally to the medical arts, and more particularly to a method of forming a slit in a reseal element for use in a needleless injection site having particular utility in relation to intravenous infusion applications.

BACKGROUND OF THE INVENTION

It is common medical practice to intravenously infuse various fluids or medicaments into a blood vessel of a patient (e.g., a vein or artery). Such infusion is typically accomplished by the insertion of a hollow introducer needle into a target blood vessel. The introducer needle is fluidly connected to one end of an elongate, flexible tube or fluid line, the opposite end of which is fluidly connected to a solution bag. The solution bag itself is typically suspended above the patient so as to allow gravity to facilitate the flow of fluid downwardly through the fluid line and into the patient's blood vessel via the introducer needle which remains operatively positioned therewithin. The fluid tube and solution bag are connected to each other via a metering apparatus which controls the infusion rate of fluid from the bag into the tube.

In many intravenous infusion assemblies, an injection site is fluidly coupled within the tubing intermediate the introducer needle and the solution bag. The injection site typically has a Y-shaped configuration and comprises a tubular main body portion having a tubular side arm portion in fluid communication therewith. The distal end of the side arm portion is fluidly connected to the solution bag via an upper segment of the tubing, with the bottom end of the main body portion being fluidly connected to the introducer needle via a lower segment of the tubing. The top end of the main body portion is itself covered by a diaphragm which is typically fabricated from rubber or a similar resilient material.

The inclusion of the injection site within the tubing allows various medications to be selectively infused into the blood vessel of the patient by the addition thereof to the solution flowing from the solution bag into the blood vessel via the upper tubing segment, injection site, lower tubing segment and introducer needle. This supplemental infusion is typically accomplished through the utilization of a conventional syringe, the needle of which pierces and is extended through the diaphragm disposed on the top end of the main body portion of the injection site. Subsequent to the expulsion of the medication from within the syringe and into the flowing solution, the needle is retracted out of the main body portion of the injection site, with the aperture created in the diaphragm due to the passage of the needle therethrough being substantially closed upon such retraction due to the resiliency of the diaphragm. As will be recognized, the incorporation of the injection site within the tubing allows various medications to be intravenously administered to the patient through the existing infusion site within the blood vessel, thus eliminating the need to subject the patient to additional needle sticks.

Though providing certain benefits to the patient, the injection sites constructed in accordance with the prior art possess certain deficiencies which detract from their overall utility. As previously explained, the use of such injection sites typically requires that the needle of the conventional syringe be extended through (i.e., puncture) the diaphragm attached to the top end of the main body portion of the injection site. However, the necessity of having to utilize a syringe with a needle to facilitate the introduction of the medication into the solution flow is undesirable due to the risk of inadvertent needle sticks.

In recognition of this deficiency, there has also been developed in the prior art needleless injection sites which incorporate a diaphragm adapted to assume open and closed configurations without having a needle inserted thereinto. Though these needleless injection sites eliminate the necessity of having to puncture the diaphragm with a needle, they also possess certain deficiencies which detract from their overall utility. Foremost of these deficiencies is the difficulty associated with disinfecting the injection site, and in particular the diaphragm thereof, subsequent to medication being infused thereinto. In this respect, after each use of the injection site the diaphragm must be cleaned, with such cleaning typically being accomplished through the application of alcohol or a similar disinfecting agent thereto. However, due to the configuration of the diaphragm, complete and effective disinfection thereof is often difficult to achieve, thus increasing the risk of the inadvertent introduction of contaminates into the solution stream upon subsequent uses of the injection site.

In an effort to overcome the deficiencies associated with the prior art injection sites, Applicant developed the needleless injection sites disclosed in the previously identified issued patents and co-pending applications which are the parent cases of the present application. In one of the parent applications preceding the present application, Applicant's needleless injection site is provided with design features which are adapted to prevent the inadvertent obstruction of the fluid flow path, and to increase the level of positive flow within the fluid flow path such that the withdrawal of a needled or non-needled introducer from within the injection site does not cause a vacuum to be pulled within a tubular fluid line connected thereto. These design features are largely embodied in the reseal member of the needleless injection site. The present invention provides a unique methodology for forming a resiliently openable and closable slit in the reseal member, and in particular the body element thereof.

SUMMARY OF THE INVENTION

In accordance with the present invention, there is provided a novel and unique method for forming a slit in a reseal element having an outer surface which is defined by a proximal end thereof, a semi-spherical inner surface portion which is defined by a dome region of the proximal end, and an annular inner surface portion which circumvents the semi-spherical inner surface portion. Further in accordance with the present invention, there is provided a cutting assembly for carrying out such method. The cutting assembly itself comprises a locator plate having a locator cavity disposed therein for receiving the reseal element. Disposed within the locator plate is a back plate of the cutting assembly which is preferably fabricated from silicone and defines the innermost end of the locator cavity.

In addition to the locator plate, the cutting assembly comprises a cutting core which is selectively movable toward and away from the locator plate. More particularly, the cutting core is movable between a slit forming position whereat it is disposed immediately adjacent the locator plate, and an unloading position whereat it is retracted away and spaced from the locator plate. Extending within the cutting core is a support fixture of the cutting assembly which is selectively extensible therefrom and retractable thereinto. More particularly, the support fixture is movable relative to the cutting core between the support position whereat the support fixture is advanced from the cutting core and protrudes therefrom, and an ejection position whereat the support fixture is retracted into the cutting core and disposed therewithin.

The support fixture includes a top end which is collectively defined by a concave recess sized to accommodate the dome region of the reseal element, and an annular rim which circumvents the recess. In the cutting assembly, the locator plate and the cutting core are oriented relative to each other such that the movement of the support fixture to its support position when the cutting core is in its slit forming position facilitates the advancement of the support fixture into the locator cavity. As such, the movement of the support fixture to its support position subsequent to the placement of the reseal element into the locator cavity and the movement of the cutting core to its slit forming position facilitates the receipt of the dome region of the reseal element into the recess and the abutment of the annular rim against the annular inner surface portion of the reseal element. The recess of the support fixture is preferably sized to have a diameter of about 0.010 inches less than the diameter of the semi-spherical inner surface portion of the reseal element such that the dome region thereof is pre-stressed when received into the recess.

In addition to the above-described components, the present cutting assembly includes a blade member which extends within the support fixture and is selectively extensible therefrom and retractable thereinto. More particularly, the blade member is movable relative to the support fixture between a cutting position whereat the blade member is advanced from the support fixture and protrudes therefrom, and a shielded position whereat the blade member is retracted into the support fixture and disposed therewithin.

The blade member of the cutting assembly defines a cutting tip, with the support fixture including a slot within the recess thereof for permitting the passage of the cutting tip into the semi-spherical inner surface portion and through the dome region to the outer surface upon the movement of the blade member to the cutting position subsequent to the placement of the reseal element into the locator cavity, the movement of the cutting core to the slit forming position, and the movement of the support fixture to the support position. In the preferred embodiment, the cutting tip is itself sized and configured such that the slit formed in the reseal element thereby does not protrude into the annular inner surface portion of the reseal element. More particularly, the cutting tip is sized and configured such that the slit has a substantially linear or straight configuration and defines opposed ends which each terminate at a distance of about 0.005 inches inwardly of the annular inner surface portion of the reseal element. As a result, a pair of web portion which each have a thickness of about 0.005 inches are defined by the dome region adjacent respective ones of the opposed ends of the slit, with the formation of such web portions being assisted by the pre-stressing of the dome region. The movement of the blade member to its cutting position when the cutting core is in its slit forming position and the support fixture is in its support position facilitates the advancement of the blade member into contact with the back plate. In this respect, the advancement of the blade member through the proximal end of the reseal element is terminated when the cutting tip makes contact with the back plate. When in contact with each other, the cutting tip of the blade member extends in generally perpendicular relation to the back plate.

In accordance with an alternative embodiment of the present invention, the support fixture includes a tubular upper portion which has a generally circular cross-sectional configuration and an inner surface which defines an axially extending bore. The upper portion defines an annular top end having a recess disposed therein which is collectively defined by an annular shoulder formed within the inner surface in close proximity to the top end and that portion of the inner surface which extends between the shoulder and the top end. The diameter of the portion of the inner surface defining the recess preferably exceeds the diameter of the remainder of the inner surface by about 0.010 inches. The recess itself has a preferred diameter of about 0.077 inches and a depth of about 0.015 inches.

The movement of the support fixture of the second embodiment to the support position subsequent to the placement of the reseal element into the locator cavity and the movement of the cutting core to the slit forming position facilitates the receipt of the dome region of the reseal element into the recess and the bore, and the abutment of the top end against the annular inner surface portion of the reseal element. Importantly, the recess is sized relative to the dome region of the reseal element such that the slit formed in the reseal element by the movement of the blade member to the cutting position does not protrude into the annular inner surface portion of the reseal element. More particularly, the slit is formed to have a substantially linear configuration defining opposed ends which each terminate at a distance of about 0.005 inches inwardly of the annular inner surface portion of the reseal element. Further, the blade member used in conjunction with the support fixture of the second embodiment is preferably formed to have a width which is substantially equal to but slightly less than the diameter of the portion of the inner surface which does not define the recess such that the blade member is supported by the upper portion of the support fixture yet axially moveable within the bore thereof.

In the preferred method of the present invention, the slit forming process is initiated with the cutting core being in its unloading position, the support fixture being in its ejection position, and the blade member being in its shielded position. When the cutting core, support fixture, and blade member are in these particular positions, the reseal element is inserted into the locator cavity of the locator plate such that the proximal end thereof is abutted against the back plate. Thereafter, the cutting core is moved to its slit forming position, which is immediately followed by the movement of the support fixture to its support position.

The movement of the support fixture to its support position results in the advancement thereof into the interior of the reseal element and the compression of the proximal end of the reseal element between the back plate and the top end of the support fixture. In particular, the dome region of the reseal element is received into the recess of the support fixture and pre-stressed due to the diameter of the recess being less than that of the semispherical inner surface portion of the reseal element defined by the dome region thereof. Additionally, the annular rim of the support fixture is abutted against the annular inner surface portion of the reseal element. When the support fixture is formed in accordance with the second embodiment of the present invention, the advancement of the support fixture into the reseal element facilitates the receipt of the dome region of the reseal element into the recess and the bore, and the abutment of the top end of the upper portion of the support fixture against the annular inner surface portion of the reseal element.

Subsequent to the movement of the support fixture to its support position, the blade member is moved from its shielded position to its cutting position. The movement of the blade member to its cutting position results in the advancement of the cutting tip thereof through the slot of the support fixture and through the proximal end of the reseal element, with such advancement being terminated by the contact of the cutting tip against the back plate. If the support fixture formed in accordance with the second embodiment is being employed, the movement of the blade member to its cutting position simply results in the advancement of the cutting tip thereof from the top end of the upper portion of the support fixture. Due to the back plate being fabricated from silicone, the cutting tip is not damaged or dulled by its contact therewith. As previously indicated, the slit is formed in the reseal element by advancing the cutting tip into the semi-spherical inner surface portion and through the dome region to the outer surface of the proximal end. The cutting of the slit in this manner (i.e., from inside to outside) maintains the concentricity of the slit within the dome region of the reseal element. In this respect, the slit must be concentric within the dome region for the reseal element to provide the required back flow protection. The pre-stressing of the dome region facilitated by its receipt into the smaller diameter recess of the support fixture of the first or second embodiments results in the formation of the above-described web portions within the dome region at each of the opposed ends of the slit. The proper sizing of the blade element also contributes to the formation of such web portions. In the reseal element, the web portions are also needed to eliminate low pressure leakage in the reseal element since high flow without leakage is desired therein.

Subsequent to the formation of the slit in the reseal element by the movement of the blade member to its cutting position, the blade member is then returned to its shielded position within the support fixture. The cutting core is then returned to its unloading position. The movement of the cutting core to its unloading position facilitates the removal of the reseal element from within the locator cavity of the locator plate. Though being removed from within the locator cavity, the reseal element remains in engagement to the support fixture. After the cutting core has been moved to its unloading position, the support fixture is returned to its ejection position wherein it is retracted into the interior of the cutting core. The movement of the support fixture to its ejection position effectuates the removal of the reseal element from thereover.

BRIEF DESCRIPTION OF THE DRAWINGS

These, as well as other features of the present invention, will become more apparent upon reference to the drawings wherein:

FIG. 1 is a cross-sectional view of a reseal element prior to the formation of a slit therein in accordance with the methodology of the present invention;

FIG. 2 is a cross-sectional view of a cutting assembly used to carry out the sequence of steps required to form the slit in the reseal element shown in FIG. 1;

FIG. 3 is a partial cross-sectional view of the cutting assembly shown in FIG. 2 illustrating the manner in which the blade member of the cutting assembly operates to facilitate the formation of the slit in the reseal element;

FIG. 4 is a partial top perspective view of the support fixture of the cutting assembly;

FIGS. 5 and 5a are partial perspective views of alternative embodiments of the blade member of the cutting assembly;

FIG. 6 is a cross-sectional view taken along line 6—6 of FIG. 3;

FIG. 7 is a cross-sectional view taken along line 7—7 of FIG. 6;

FIG. 8 is a partial top perspective view of the reseal element subsequent to the formation of the slit therewithin in accordance with the methodology of the present invention.

DETAILED DESCRIPTION OF THE PREFERRED EMBODIMENTS

Figure 9:
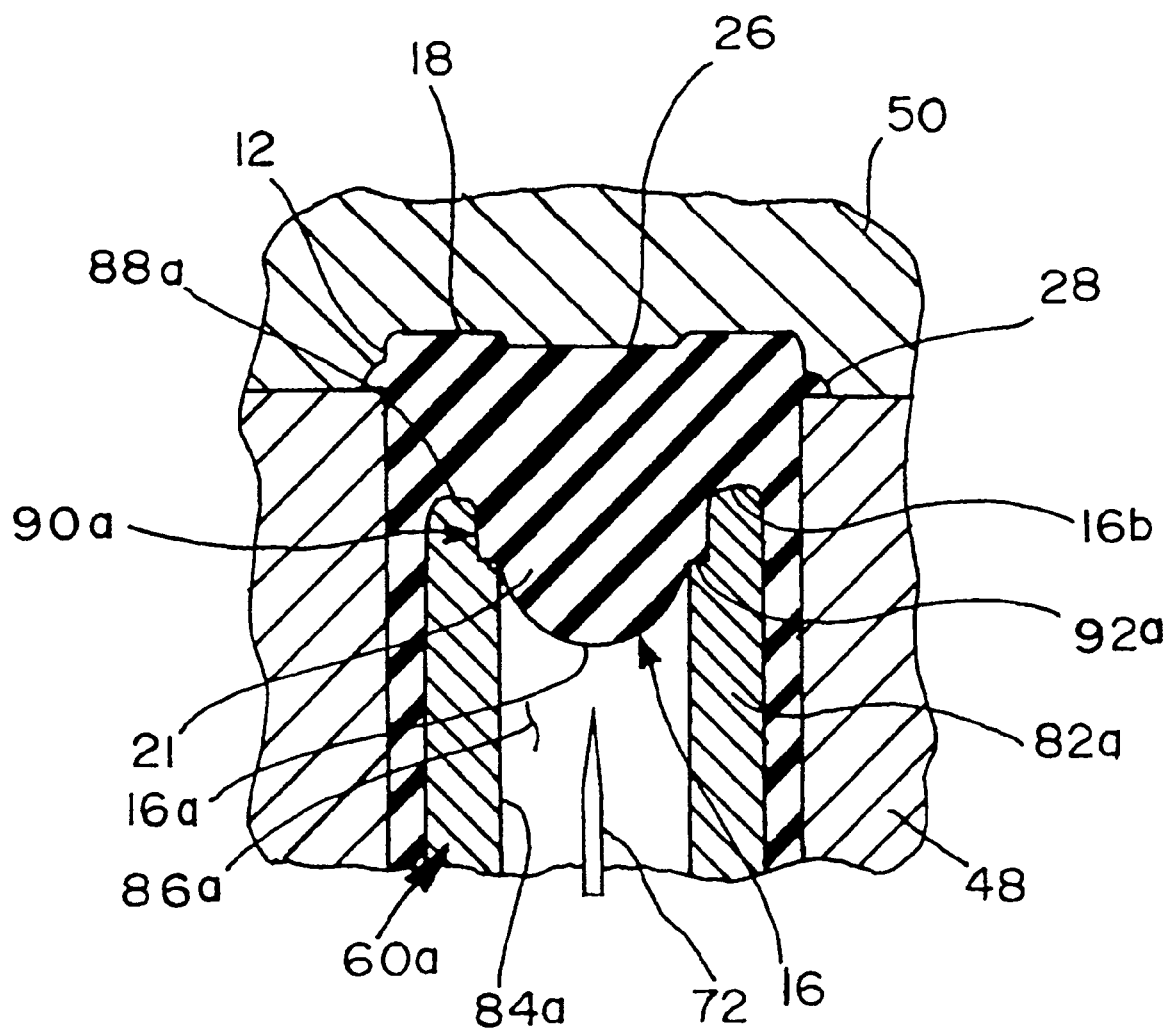
FIG. 9 is a partial cross-sectional view of a second embodiment of the support fixture of the cutting assembly.

Referring now to the drawings wherein the showings are for purposes of illustrating a preferred embodiment of the present invention only, and not for purposes of limiting the same, FIG. 1 illustrates a reseal element 10 prior to the formation of a resiliently openable and closable slit therein in accordance with the methodology of the present invention. The reseal element 10 is substantially similar, both structurally and functionally, to the body of the reseal member described in the preceding parent applications. In this respect, the reseal element 10 includes a proximal end 12 and a distal end 14, with the proximal end 12 having an inner surface 16 and an outer surface 18. The proximal end 12 is itself defined by a generally cylindrical proximal portion 20 of the reseal element 10, which also includes a generally cylindrical distal portion 22. The proximal and distal portions 20, 22 are separated by a beveled shoulder 24 formed therebetween, and are sized such that the diameter of the distal portion 22 exceeds the diameter of the proximal portion 20.

In the reseal element 10, the inner surface 16 of the proximal end 12 includes a generally semi-spherical portion 16a which is defined by an inner dome region 21 of the proximal end 12, and an annular portion 16b which circumvents the base of the semi-spherical portion 16a. Additionally, formed in the outer surface 18 of the proximal end 12 is a circularly configured depression 26 which is centrally positioned within the outer surface 18. Further, formed on the proximal portion 20 is a centering ring 28 which extends thereabout and has a generally wedge-shaped cross-sectional configuration.

The distal end 14 of the reseal element 10 is defined by an annular flange 30 which is formed on the distal portion 22 and extends radially inward and outward relative thereto. Formed on the inner peripheral edge of the flange 30 is an enlarged bead 32. In the reseal element 10, the distal portion 22 is not of a uniform wall thickness, but rather includes a section of increased thickness adjacent the flange 30 which is separated from the remainder of the distal portion 22 by a beveled shoulder 34.

Referring now to FIGS. 7 and 8, the slit forming methodology of the present invention, as will be described in more detail below, is carried out upon the reseal element 10 for purposes of forming a resiliently openable and closable slit 36 therewithin. More particularly, the slit 36 is formed in the proximal end 12 of the reseal element 10 and extends from the outer surface 18 to the apex of the semi-spherical portion 16a of the inner surface 16. The slit 36 extends along the axis of the reseal element 10, with the end thereof extending to the outer surface 18 being disposed within the depression 26. The slit 36 is formed to have a width such that the opposed ends thereof do not protrude beyond the periphery of the depression 26, or into the annular portion 16b of the inner surface 16.

The slit 36 is formed within the proximal end 12 of the reseal element 10 through the use of a cutting machine 38 shown in FIG. 2. The cutting machine 38 is provided with at least one cutting assembly 40 which comprises a stationary locator plate 42. The locator plate 42 itself comprises an upper section 44 and a cylindrically configured lower section 46 which is attached to the generally planar bottom surface of the upper section 44 in close proximity to the peripheral edge thereof. The lower section 46 of the locator plate 42 defines a generally planar bottom end 45 which is circumvented by a beveled shoulder 47. Disposed within the lower section 46 is a locator cavity 48 which has a configuration generally corresponding to that of the reseal element 10. The closed, innermost end of the locator cavity 48 is defined by a cylindrically configured back plate 50 of the cutting assembly 40 which is disposed within the upper section 44 of the locator plate 42 and protrudes a small distance into the lower section 46 thereof. The back plate 50 is oriented within the locator plate 42 so as to be in coaxial alignment with the locator cavity 48 disposed within the lower section 46. Additionally, the back plate 50 is preferably fabricated from silicone, and is used for reasons which will be discussed in more detail below.

In addition to the locator plate 42, the cutting assembly 40 comprises an elongate, tubular cutting core 52 which has a generally cylindrical configuration. The cutting core 52 defines a generally planar top end 54 which is circumvented by a beveled shoulder 56. Disposed within the top end 54 at the axis or center thereof is a circularly configured opening 58 which extends axially into communication with the hollow interior of the cutting core 52. The cutting core 52 is selectively moveable relative to the lower plate 42 between a slit forming position (as shown in FIG. 2) wherein the cutting core 52 is disposed immediately adjacent the locator plate 42 (i.e., the top end 54 is abutted against the bottom end 45 of the lower section 46) and an unloading position whereat the cutting core 52 is retracted away from the locator plate 42 (i.e., the top end 54 is disposed in spaced relation to the bottom end 45). When the cutting core 52 is in its slit forming position, the opening 58 thereof is coaxially aligned with the lower cavity 48.

Referring now to FIGS. 2–4, the cutting assembly 40 further comprises an elongate, tubular support fixture 60 which extends within the cutting core 52 and is selectively extensible therefrom and retractable thereinto. More particularly, the support fixture 60 is movable relative to the cutting core 52 between a support position whereat the support fixture 60 is advanced from the cutting core 52 and protrudes therefrom, and an ejection position (as shown in FIG. 2) whereat the support fixture 60 is retracted into the cutting core 52 and disposed within the interior thereof.

As best seen in FIG. 4, the support fixture 60 includes a top end 62 which is collectively defined by a semi-spherical or concave recess 64 which is adapted to accommodate the dome region 21 of the reseal element 10, and an annular rim 66 which circumvents the recess 64. Formed within the apex of the recess 64 is an elongate, arcuately shaped slot 68 which communicates with the hollow interior of the support fixture 60. In the support fixture 60, the recess 64 is preferably sized to have a diameter of about 0.010 inches less than the diameter of the semi-spherical inner surface portion 16a of the inner surface 16 for reasons which will be discussed in more detail below.

When the support fixture 60 is in its ejection position as shown in FIG. 2, the rim 66 defined by the top end 62 is substantially flush or continuous with the top end 54 of the cutting core 52. The movement of the support fixture 60 to its support position facilitates the axial advancement of the top end 62 thereof into the interior of the locator cavity 48. The diameter of the opening 58 within the cutting core 52 is sized so as to slightly exceed the diameter of the support fixture 60, thus allowing the support fixture 60 to be slidably movable therewithin. The movement of the support fixture 60 between its support and ejection positions is facilitated by a cylinder member 70 which extends into the hollow interior of the cutting core 52 and is attached to the base of the support fixture 60.

The cutting assembly 40 further comprises an elongate blade member 72 which extends within the interior of the support fixture 60 and is selectively extensible therefrom and retractable thereinto. More particularly, the blade member 72 is movable relative to the support fixture 60 between a cutting position (as shown in FIG. 6) whereat the blade member 72 is advanced from the support fixture 60 and protrudes therefrom, and a shielded position (as shown in FIGS. 2 and 3) whereat the blade member 72 is retracted into the support fixture 60 and disposed within the interior thereof.

As best seen in FIGS. 5 and 6, the blade member 72 defines a cutting tip or edge 74 which has a chisel-like configuration. When the blade member 72 is in its shielded position, the cutting tip 74 is disposed within the interior of the support fixture 60 inwardly of the slot 68 disposed within the top end 62 as seen in FIG. 3. When the blade member 72 is in its cutting position, the cutting tip 74 protrudes beyond the rim 66 of the top end 62 as seen in FIG. 6. The movement of the blade member 72 between its shielded and cutting positions is facilitated by a movable support post 76 which is attached to the end of the blade member 72 opposite the cutting tip 74 thereof, and slidably received into the hollow interior of the support fixture 60. The blade member 72 is normally biased to its shielded position by a biasing spring 78 which is secured to the support post 76. As will be recognized, the blade member 72 is advanced through the slot 68 within the top end 62 when moved from its shielded position to its cutting position.

Referring now to FIG. 5a, as an alternative to the blade member 72, the cutting assembly 40 may be provided with a blade member 72a which defines a pointed or wedge-shaped cutting tip 74a as an alternative to the chisel-like cutting tip 74 of the blade member 72. Additionally, in the blade member 72a, cutting surfaces are defined at each of the opposed side edges thereof.

Having thus described the components of the cutting assembly 40, a preferred method of forming the slit 36 in the reseal element 10 will now be described with particular reference to FIGS. 2, 3 and 6. The slit forming process is initiated with the cutting core 52 being in its unloading position, the support fixture 60 being in its ejection position, and the blade member 72 being in its shielded position. When the cutting core 52, support fixture 60, and blade member 72 are in these particular positions, the reseal element 10 is inserted into the locator cavity 48 of the stationary locator plate 42 such that the proximal end 12 thereof is abutted against the back plate 50. Thereafter, the cutting core 52 is moved to its slit forming position whereat the top end 54 thereof is abutted against the bottom end 45 of the lower section 46 of the locator plate 42.

In the present method, the movement of the cutting core 52 to its slit forming position is immediately followed by the movement of the support fixture 60 to its support position. Such movement of the support fixture 60 results in the advancement thereof into the interior of the reseal element 10. Such advancement is continued until such time as the proximal end 12 of the reseal element 10 is compressed between the back plate 50 and the top end 62 of the support fixture 60. More particularly, upon the movement of the support fixture 60 to its support position, the dome region 21 of the reseal element 10 is received into the recess 64 within the top end 62 and pre-stressed (i.e., compressed radially inwardly) due to the diameter of the recess 64 being less than that of the semi-spherical inner surface portion 16a defined by the dome region 21. In addition to the dome region 21 being received into the recess 64 in the aforementioned manner, the annular rim 66 of the top end 62 is abutted against the annular inner surface portion 16b.

Subsequent to the movement of the support fixture 60 to its support position, the blade member 72 of the cutting assembly 40 is moved from its shielded position to its cutting position. The movement of the blade member 72 to its cutting position results in the advancement of the cutting tip 74 through the slot 68 of the support fixture 60 and upwardly through the proximal end 12 of the reseal element 12. Such upward advancement of the blade member 72 is terminated by the contact of the cutting tip 74 thereof against the back plate 50. When such contact is made, the blade member 72 extends in generally perpendicular relation to the back plate 50. Due to the back plate 50 being fabricated from silicone, the cutting tip 74 penetrates slightly thereinto, and thus is not damaged or dulled by its contact with the back plate 50.

In forming the slit 36 within the reseal element 10, the cutting tip 74 of the blade member 72 is initially advanced into the semi-spherical inner surface portion 16a, and thereafter through the dome region 21 to the outer surface 18 of the proximal end 12. Importantly, the cutting of the slit 36 in this manner (i.e., from inside to outside) maintains the concentricity of the slit 36 within the dome region 21 of the reseal element 10. The concentric positioning of the slit 36 within the dome region 21 provides the required back flow protection within the reseal element 10.

In addition to the slit 36 being concentrically positioned within the dome region 21 due to the initial advancement of the blade member 72 into the semi-spherical inner surface portion 16a, the pre-stressing of the dome region 21 facilitated by its receipt into the smaller diameter recess 64 of the support fixture 60 results in the formation of a pair of web portions 80 within the dome region 21 at each of the opposed ends of the slit 36, as seen in FIG. 7. Each of the web portions 80 is preferably sized so as to have a thickness T of about 0.005 inches. As such, the opposed ends of the slit 36 each terminate at a distance of about 0.005 inches inwardly of the annular inner surface portion 16b. The proper sizing of the blade element 74, 74a also contributes to the formation of the web portions 80 within the dome region 21. In the reseal element 10 having the slit 36 formed therein, the web portions 80 function to eliminate low pressure leakage.

Subsequent to the formation of the slit 36 in the reseal element 10 by the movement of the blade member 72 to its cutting position, the blade member 72 is then returned to its shielded position within the support fixture 60. The cutting core is then returned to its unloading position whereat it is disposed in spaced relation to the locator plate 42. The movement of the cutting core 52 to its unloading position facilitates the removal of the reseal element 10 (now including the slit 36 formed therein) from within the locator cavity 48 of the locator plate 42. Though being removed from within the locator cavity 48, the reseal element 10 remains in engagement to the support fixture 60. After the cutting core 52 has been moved to its unloading position, the support fixture 60 is returned to its ejection position wherein it is retracted into the interior of the cutting core 52. The movement of the support fixture 60 to its ejection position effectuates the removal of the reseal element 10 from thereover, thus allowing the reseal element 10 to be simply removed from upon the top end 54 of the cutting core 52.

The cutting machine 38 is provided with various components as are needed to facilitate the movement of the cutting core 52 between its slit forming and unloading positions, the movement of the support fixture 60 between its support and ejection positions, and the movement of the blade member 72 between its shielded and cutting positions. It is contemplated that the above-described slit forming method will be implemented on the cutting machine 38 which may include multiple cutting assemblies 40 disposed therein in a generally circular configuration so as to facilitate the simultaneous cutting of multiple reseal elements 10.

Referring now to FIG. 9, there is depicted a support fixture 60a which is constructed in accordance with a second embodiment of the present invention and may be incorporated into the cutting assembly 40 as an alternative to the previously described support fixture 60. As will be discussed in more detail below, the support fixture 60a is substantially similar to the previously described support fixture 60, with the primary structural differences lying in the configuration of the top portion of the support fixture 60a.

In the second embodiment, the support fixture 60a includes a tubular upper portion 82a which has a generally circular cross-sectional configuration and an inner surface 84a which defines an axially extending bore 86a. The upper portion 82a also defines an annular top end 88a. Disposed within the top end 88a is a recess 90a. The recess 90a is collectively defined by an annular shoulder 92a formed within the inner surface 84a in close proximity to the top end 88a and that portion of the inner surface 84a which extends between the shoulder 92a and the top end 88a. In the second embodiment, the diameter of the portion of the inner surface 84a which defines the recess 90a exceeds the diameter of the remainder of the inner surface 84a by about 0.010 inches. In this respect, the recess 90a has a preferred diameter of about 0.077 inches and a preferred depth of about 0.015 inches.

When the support fixture 60a is integrated into the cutting assembly 40, the movement of the support fixture 60a to the support position subsequent to the placement of the reseal element 10 into the locator cavity 48 and the movement of the cutting core 52 to the slit forming position facilitates the receipt of the dome region 21 of the reseal element 10 into the recess 90a and the bore 86a, and the abutment of the top end 88a against the annular inner surface portion 16b of the reseal element 10 in the manner shown in FIG. 9. Importantly, the recess 90a is sized relative to the dome region 21 of the reseal element 10 such that the slit 36 formed in the reseal element 10 by the movement of the blade member 72 to the cutting position does not protrude into the annular inner surface portion 16b of the reseal element 10. The diameter of the dome region 21 slightly exceeds the diameter of the recess 90*a* such that a pre-stress is applied to the dome region 21 when the same is received into the recess 90*a* and bore 86*a*. Due to a portion of the dome region 21 being received into the recess 90*a*, the slit 36 formed in the reseal element 10 by the movement of the blade member 72 to its cutting position has a substantially linear configuration and defines opposed ends which each terminate at a distance of about 0.005 inches inwardly of the annular inner surface portion 16*b* of the reseal element 10. Further, the upper portion 82*a* of the support fixture 60*a* is preferably formed such that the width of the blade member 72 is substantially equal to but slightly less than the diameter of the portion of the inner surface 84*a* which does not define the recess 90*a*. As a result, the blade member 72 is supported by the upper portion 82*a* of the support fixture 60*a* and axially movable within the bore 86*a* thereof.

Additional modifications and improvements of the present invention may also be apparent to those of ordinary skill in the art. Thus, the particular parts and steps described and illustrated herein are intended to represent only one embodiment of the present invention, and are not intended to serve as limitations of alternative devices within the spirit and scope of the invention.

What is claimed is:

1. A method of forming a slit in a reseal element having an outer surface defined by a proximal end thereof, a semi-spherical inner surface portion defined by a dome region of the proximal end, and an annular inner surface portion which circumvents the semi-spherical inner surface portion through the use of a cutting assembly including a locator plate having a locator cavity disposed therein, a cutting core, a support fixture, and a blade member, the method comprising the steps of:

(a) inserting the reseal element into the locator cavity of the locator plate;

(b) (1) moving the cutting core from an unloading position whereat it is retracted away and spaced from the locator plate to a slit forming position whereat it is disposed immediately adjacent the locator plate; and (2) moving the support fixture relative to the cutting core from an ejection position whereat the support fixture is retracted into the cutting core and disposed therewithin to a support position whereat the support fixture is advanced from the cutting core into contact with the semi-spherical and annular inner surface portions of the reseal element to pre-stress the dome region of the reseal element; and (c) advancing the blade member through the proximal end of the reseal element to form the slit therein.

2. The method of claim 1 wherein:

the support fixture includes a top end which is collectively defined by a concave recess having a diameter which is slightly less than the diameter of the semi-spherical inner surface portion of the reseal element, and an annular rim which circumvents the recess; and step (b) comprises advancing the support fixture into the reseal element such that the dome region of the reseal element is received into the recess and the annular rim is abutted against the annular inner surface portion of the reseal element.

3. The method of claim 1 wherein:

the support fixture includes a tubular upper portion which defines an annular top end and an axially extending bore, and a circularly configured recess which is disposed within the top end; and step (b) comprises advancing the support fixture into the reseal element such that the dome region of the reseal element is received into the recess and the bore, and the top end is abutted against the annular inner surface portion of the reseal element.

4. The method of claim 1 wherein:

the blade member defines a cutting tip; and step (c) comprises advancing the cutting tip into the semi-spherical inner surface portion and through the dome region to the outer surface.

5. The method of claim 4 wherein step (c) comprises forming the slit to have a substantially linear configuration with opposed ends and a length wherein a pair of web portions which each have a thickness of about 0.005 inches are defined by the dome region adjacent respective ones of the opposed ends of the slit.

6. The method of claim 4 wherein:

the cutting assembly further includes a back plate which is disposed within the locator plate and defines the innermost end of the locator cavity; and step (c) comprises advancing the cutting tip through the proximal end of the reseal element until such time as the cutting tip makes contact with the back plate.

7. The method of claim 1 further comprising the step of:

(d) ejecting the reseal element having the slit formed therein from the cutting assembly.

8. The method of claim 7 wherein the blade member extends within the support fixture and step (c) comprises:

(1) moving the blade member relative to the support fixture from a shielded position whereat the blade member is retracted into the support fixture and disposed therewithin to a cutting position whereat the blade member is advanced from the support fixture through the proximal end of the reseal element; and (2) moving the blade member from the cutting position to the shielded position.

9. The method of claim 8 wherein step (d) comprises:

(1) moving the cutting core from the slit forming position to the unloading position; and (2) moving the support fixture from the support position to the ejection position.

* * * * *